United States Patent
Yamaguchi et al.

(10) Patent No.: US 6,994,734 B2
(45) Date of Patent: Feb. 7, 2006

(54) AQUEOUS LIQUID COMPOSITION OF FLUORESCENT BRIGHTENER EXCELLENT IN DYEING CHARACTERISTICS

(75) Inventors: Toru Yamaguchi, Saitama (JP); Nobutaka Yamamoto, Okegawa (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 46 days.

(21) Appl. No.: 10/472,322

(22) PCT Filed: Mar. 20, 2002

(86) PCT No.: PCT/JP02/02674

§ 371 (c)(1),
(2), (4) Date: Sep. 18, 2003

(87) PCT Pub. No.: WO02/077106

PCT Pub. Date: Oct. 3, 2002

(65) Prior Publication Data

US 2004/0111812 A1    Jun. 17, 2004

(30) Foreign Application Priority Data

Mar. 22, 2001   (JP)   ............. 2001-082280

(51) Int. Cl.
*D06P 1/66*   (2006.01)
*D06P 3/60*   (2006.01)

(52) U.S. Cl. ................... 8/554; 8/648; 8/919
(58) Field of Classification Search ........... 8/648, 8/919, 554
See application file for complete search history.

(56) References Cited

U.S. PATENT DOCUMENTS 3,479,349 A   11/1969  Allison et al. .......... 260/240
4,466,900 A * 8/1984  Horlacher et al. ...... 252/301.23

FOREIGN PATENT DOCUMENTS

| GB | 1241400 | * | 8/1971 |
| GB | 1243479 | * | 8/1971 |
| JP | 33-7639 |   | 8/1958 |
| WO | 02/060883 |   | 8/2002 |

* cited by examiner

*Primary Examiner*—Margaret Einsmann
(74) *Attorney, Agent, or Firm*—Neilds & Lemack

(57) ABSTRACT

An aqueous liquid composition characterized by containing an alkali salt, an alkali metal salt, an alkali earth metal salt or an ammonium salt of a compound represented by the following formula (1).

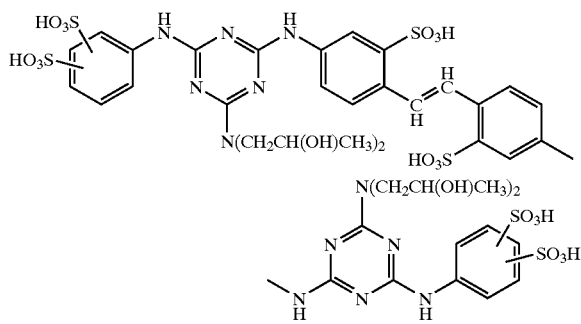

in the form of free acid in an amount of 10–40 mass % and inorganic salt in an amount of 1.1–10 mass % can easily be produced without a desalting process or the like which has been included in a conventional process and it has an excellent storage stability and excellent fluorescent brightening effect.

3 Claims, No Drawings

AQUEOUS LIQUID COMPOSITION OF FLUORESCENT BRIGHTENER EXCELLENT IN DYEING CHARACTERISTICS

TECHNICAL FIELD

The present invention relates to a concentrated aqueous liquid composition of fluorescent brightener and to a method for using the same. More particularly, it relates to a concentrated aqueous liquid composition which contains a fluorescent brightener having a specific structure and has excellent storage stability at low temperature and also at high temperature.

BACKGROUND OF THE INVENTION

As for dyeing with a fluorescent brightener, it is usual that conventionally available powdery or granular dye is once dissolved in hot water and is subjected to dyeing. On the other hand, in paper factories or dyeing factories, automation and FA have progressed and there has been a demand for liquid products which are able to cope with automated measurement systems.

Aqueous solution of fluorescent brightener has a disadvantage that, due to the presence of inorganic salts which are by-produced during the manufacture of fluorescent brightener, stability at low temperature and at high temperature is low whereby crystals, etc. are separated out. In order to prevent that, inorganic salts contained in aqueous solution of fluorescent brightener are decreased using semipermeable membrane or like to enhance the stability. For example, JP-A-58-65760 and JP-A-60-158266 disclose a method where concentration of salts in aqueous solution of fluorescent brightener of a stilbene derivative is decreased to prepare a concentrated aqueous solution is manufactured.

With regard to a method where no semipermeable membrane is used, a method, for example, JP-A-58-222156 discloses where insoluble or hardly-soluble metal salt of stilbene derivative is made to react with lower hydroxylamine in the presence of carbonate ion and insoluble substance is removed from the reaction mixture to prepare a stable concentrated aqueous solution containing the stilbene derivative as a fluorescent brightener.

Further, JP-A-57-123262 discloses that a tetraalkylammonium compound such as tetramethylammonium, tetraethylammonium or tetrapropylammonium is added to aqueous solution of sodium salt of stilbene derivative for example to convert the sodium salt to tetraalkylammonium salt to prepare a fluorescent brightener mainly comprising tetraammonium salt and thereby a part of specific dyes becomes to exhibit higher solubility than sodium salt, etc. Furthermore, JP-A-62-273266 discloses a method as an improved method of the method disclosed in JP-A-57-123262, wherein sodium salt of stilbene derivative is changed to a salt with a tetraammonium compound having hydroxyl group such as choline, desalted using a compressed filtering apparatus and then a solubilizing agent such as urea is added thereto to manufacture a stable concentrated aqueous solution containing the stilbene derivative as a fluorescent brightener.

Incidentally, the stilbene derivative used in the present invention and represented by the formula (1) mentioned later is disclosed in JP-A-58-22156, British Patent 1,243,479 and Belgian Patent 719065 for its structure. Further, in British Patent 1,243,479 and Belgian Patent 719065, the compound of the formula (1) is also disclosed together with other stilbene derivatives and the synthetic method and the use as fluorescent brightening for paper, etc are disclosed. However, in those patents, there is no disclosure relating to preparations of a dyeing solution (including a coating liquid) or a concentrated aqueous solution which is prepared in such a manner that the solution is able to be directly used for dyeing.

Since anionic dye is used in an ink for ink jet printers using a water-soluble dye, there are many cases in a high quality-recording paper for ink jet printers that, in order to suppress the blotting of ink on the paper, a cationic ink fixing agent or water resisting agent is used during the manufacture of the recording paper. In addition, since clear coloration is demanded for the recording paper, there has been a demand for a degree of whiteness of high quality. Therefore, recording paper dyed in high whiteness is manufactured using various kinds of fluorescent brighteners. With regard to the fluorescent brightener used at that time, an anionic water-soluble fluorescent brightener is frequently used due to the characteristic of the manufacturing process. However, when the above-mentioned cationic fixing agent and anionic fluorescent brightener are used together, the ink fixing agent is combined with the fluorescent brightener in a solution to make them insoluble in water and, as a result, there is a disadvantage of causing the phenomena that crystals are separated out and that high whiteness demanded in the dyeing is not achieved.

As mentioned above, it was not possible to prepare any stable concentrated aqueous solution containing high concentration of stilbene derivative used for fluorescent brightening of cellulose such as paper, pulp or cotton unless excessive steps for the purpose of desalting, etc. are applied. Thus, excessive step, solubilizing agent, etc. are always necessary, for example, as shown in JP-A-58-65760that desalting with semipermeable membrane which requires time and cost is carried out; as shown in JP-A-58-222156 that sodium salt of stilbene derivative is once converted to an insoluble salt and then converted to a lower hydroxylamine salt and the precipitated inorganic salt is removed; or, as shown in JP-A-62-273266 that, after sodium salt of stilbene derivative is once converted to a salt with choline or the like, desalting is conducted and then a solubilizing agent is added to give a stable concentrated aqueous solution. Further, in fluorescent brightening of high quality recording paper for ink jet printers, a fluorescent brightener having a high fluorescent brightening effect is demanded even when a cationic fixing agent is used together. Therefore, there has been a demand for developing a concentrated aqueous solution which contains a high concentration of fluorescent brightener such as stilbene derivative, shows excellent storage stability at low and high temperatures, is able to be manufactured easily and at low cost and further satisfies the following requirements that 1. it shows an excellent brightening effect when it is used for fluorescent brightening for cellulose, etc.;
2. it achieves an excellent fluorescent brightening effect even when used together with cationic ink fixing agent for fluorescent brightening of recording paper, etc. for ink jet printers;
3. it has excellent fixing property and water fastness property when used for fluorescent brightening of recording paper, etc. for the ink jet printers; etc.

DISCLOSURE OF THE INVENTION

The present inventors have repeatedly carried out extensive studies for solving the above-mentioned problems and, quite unexpectedly, they have found that, in the case of the stilbene derivative represented by the following formula (1), synthesized sodium salt, etc. are directly able to be made into a stable concentrated aqueous liquid composition without conducting a desalting step and have achieved the present invention has been achieved. Thus, the present invention relates to:

(1) an aqueous liquid composition characterized by containing 10–40% by mass of an alkali salt of a compound represented by the following formula (1)

The aqueous liquid composition of the present invention means the one where the alkali salt and inorganic acid salt of the compound of the above formula (1) is contained in an aqueous medium and, in some cases, it may contain organic solvent or/and other solubilizer, etc. for improving the solubility of the compound of the formula (1) in water. Further, the aqueous liquid composition may be either an aqueous liquid composition where the components are entirely dissolved or an aqueous liquid composition where a

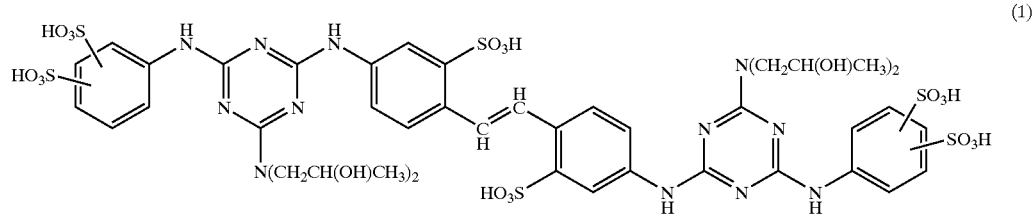

(1)

in a form of free acid and in that the content of inorganic salt is 1.1–10% by mass.

(2) an aqueous liquid composition characterized by containing 10–40% by mass of an alkali salt of a compound represented by the following formula (2)

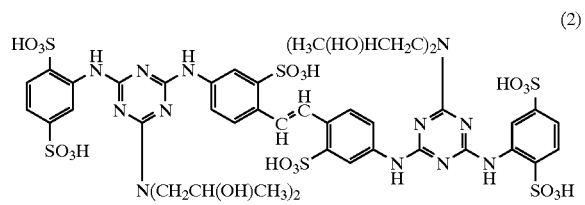

(2)

in a form of free acid and in that the content of inorganic salt is 1.1–10% by mass.

(3) the aqueous liquid composition according to the above (1) or (2), wherein the alkali salt is an alkaline metal salt, an alkaline earth metal salt or an ammonium salt.

(4) the aqueous liquid composition according to the above (1), wherein it contains substantially no organic solvent and solubilizer.

(5) a method for fluorescent brightening of cellulose characterized by using the aqueous liquid composition as mentioned in the above (3).

(6) a method for fluorescent brightening of ink jet recording paper which is characterized by using the aqueous liquid composition mentioned in the above (3) and a cationic ink fixing agent together.

(7) use of an aqueous liquid composition containing 10–40% by mass of alkali salt of the compound represented by the formula (1) mentioned in the above (1) or alkali salt of the compound represented by the formula (2) mentioned in the above (2) in a form of free acid and 1.1–10% by mass of inorganic salt as a fluorescent brightener.

BEST MODE FOR CARRYING OUT THE INVENTION

The aqueous liquid composition of the present invention will now be described in detail.

part of the components are dispersed so as to be an aqueous suspension composition. Preferably, it is an aqueous liquid composition where the components are entirely dissolved to form an aqueous solution. An aqueous liquid composition cotaining substancially no organic solvent is usually sufficient to where organic solvent or other solubilizer are not substantially contained.

Although there is no particular limitation for the substituted positions of the two sulfonic acid groups on anilino groups on both ends in the compound of the above formula (1) used in the present invention, they are usually 2- and 4-positions or 2- and 5-positions and preferably 2- and 5-positions. The compound having sulfonic acid groups at 2- and 5-positions on the aniline groups is represented by the above formula (2).

The alkali salt of the compound of the above formula (1), includes an alkaline metal salt, alkaline earth metal salt and an ammonium salt. An alkaline metal salt is preferred and lithium salt and sodium salt are more preferred.

Concentration of the alkali salt of the compound of the above formula (1) (as hereunder, the alkali salt is referred to just "the compound of the formula (1)" unless otherwise mentioned) in the aqueous liquid composition of the present invention is 10–40% by mass, preferably about 10–20% by mass or, more preferably, about 12% by mass to 20% by mass.

The organic solvent and other solubilizer which may be contained in the aqueous liquid composition of the present invention includes hydrotropic agents such as alcohols (e.g., methanol and ethanol), glycols (e.g., ethylene glycol, diethylene glycol and propylene glycol), acid amides (e.g., urea, N-substituted urea and ε-caprolactam), water-soluble high-molecular substances (e.g., polyvinyl alcohol, polyethylene glycol and solubilized starch), pH buffers, surface-active agents, etc. and each of them may be used solely or two or more thereof may be mixed and used.

Remainder which is other than the above-mentioned components in the aqueous liquid composition of the present invention is water.

The compound of the above formula (1) used in the aqueous liquid composition of the present invention is obtained, for example, by reacting 1 mole of 4,4'-diaminostilbene-2,2'-disulfonic acid with 2 moles of cyanuric chloride, reacting thus obtained compound with 2 moles of anilinedisulfonic acid and then reacting thus obtained the resulting compound with 2 moles of di-2-propanolamine. Alternatively, it can be obtained by reacting 2 moles of anilinedisulfonic acid with 2 moles of cyanuric chloride, reacting thus obtained compound with 1 mole of 4,4'-diaminostilbene-2,2'-disulfonic acid and then reacting obtained compound with 2 moles of di-2-propanolamine. In that case, the reaction is carried out by adjusting the amount of the solvent used so that the compound of the formula (1) is present in the above concentration in the final reaction solution whereby the synthetic reaction solution for the compound of the formula (1) can be used directly as the aqueous liquid composition of the present invention. It is also possible that the resulting reaction solution is concentrated so as to increase the concentration of the compound of the formula (1) to the above concentration range and is used as the aqueous liquid composition of the present invention.

In case the compound of the formula (1) obtained by the above methods is taken out from the reaction solution, it may be taken out as crystals of free acid by separating out with hydrochloric acid, sulfuric acid, nitric acid or the like or may be taken out as crystals of alkaline metal salt or alkaline earth metal salt such as sodium salt, potassium salt or calcium salt by salting out with inorganic salt such as sodium chloride, potassium chloride, calcium chloride or sodium sulfate.

The free acid of the compound of the formula (1) taken out is dissolved in water together with a desired amount of sodium hydroxide or, alternatively, the alkaline metal salt or the alkaline earth metal salt of the resulting compound of the formula (1) is dissolved in water so as to make the concentration of the compound of the formula (1) within the above-mentioned concentration range whereupon the aqueous liquid composition of the present invention is obtained.

Content of the inorganic salt such as sodium chloride or sodium sulfate in the aqueous liquid composition of the present invention is 1.1–10% by mass or, preferably, 1.1–5% by mass. Content of the inorganic salt in the present invention is the total content of alkaline metal chloride or alkaline earth metal chloride (such as sodium chloride, potassium chloride and calcium chloride) and alkaline metal sulfate (such as sodium sulfate) or alkaline earth metal sulfate and, most typically, it means contents of sodium chloride and sodium sulfate. Content of sodium chloride, etc. is the amount which is measured by titration of chlorine anion with silver nitrate or by ion chromatography followed by converting into the amount of sodium chloride. Content of sodium sulfate, etc. is the amount where sulfate anion is measured by ion chromatography followed by converting into the amount of sodium sulfate. When the content of inorganic salt in the aqueous liquid composition is more than 10% by mass, the storage stability goes worse because crystals of the dye are separated out. Therefore it is not preferable. In the aqueous liquid composition of the present invention, said stability is high and no crystal is separated out although inorganic salts are present in the composition provided that the inorganic salt content is within the above range.

The aqueous liquid composition of the present invention is suitable for fluorescent brightening of cellulose. There is no particular limitation for the cellulose to be subjected to fluorescent brightening. It is able to apply fluorescent brightening to all things so far as they are made of cellulose and, usually, it is used for fluorescent brightening of materials of a cellulose type. When the aqueous liquid composition of the present invention is used for fluorescent brightening of materials of a cellulose type, the aqueous liquid composition of the present invention may be used in such a manner that the amount of the compound of the formula (1) is 0.01–4% by mass to the material of a cellulose type.

The material of a cellulose type includes papers, pulp, cotton, etc., and papers and pulp are particularly preferred. Method for coloration (fluorescent brightening method) of paper and pulp is roughly classified into an internal addition method wherein a fluorescent brightener is added during the process from beating of pulp to paper manufacture to colorize and an external addition method wherein a fluorescent brightener is added to a size press liquid in a size press process after the paper manufacture. Besides those, there is a method where an coating liquid prepared from fluorescent brightener, inorganic white pigment, binder, etc. is overcoated on the surface of paper. The aqueous liquid composition of the present invention is able to be applied to any of those methods.

The internal addition method, pulp is firstly beaten to a predetermined beating degree using a pulper, a refiner or the like to give a pulp slurry, the aqueous liquid composition of the present invention is added thereto usually at 10–40° C. so that and the amount of the compound of the formula (1) is 0.01–4.0% by mass to the mass of dry paper, then common sizing agent, sulfate band, paper reinforcing agent, fixing agent, etc. are added thereto if necessary and subjected to paper manufacturing step and drying step by conventional methods to give fluorescently brightened paper.

In the size press in the external addition method, pulp is firstly beaten to a predetermined beaten degree with a pulper, a refiner or the like, then a usual filler, a sizing agent, a sulfate band, a fixing agent, etc. are appropriately added thereto and subjected to paper manufacture by conventional method. After that, in a step of drying using a cylinder drier, a size press coating liquid containing the aqueous liquid composition of the present invention is coated with a size press machine placed in the middle part of the cylinder driers which are aligned in many numbers (usually, 20–60) and then dried to give fluorescently brightened paper. The size press coating liquid mentioned above is prepared by appropriately mixing of the aqueous liquid composition of the present invention with starch, PVA, CMC, surface sizing agent, water, etc. Content of the aqueous liquid composition in the size press coating liquid is usually 0.01–6.0% by mass in terms of the compound of the formula (1) to the total amount of the size press coating liquid and the coating amount of the size press coating liquid is usually 0.5–3 g/m$^2$ (dry mass) to dry paper.

In an overcoating of the external addition method, pulp is firstly beaten to a predetermined beaten degree with a pulper, a refiner or the like, then a usual filler, sizing agent, sulfate band, fixing agent, etc. are appropriately added thereto and subjected to paper manufacture by conventional method. A coating liquid containing the aqueous liquid composition of the present invention is coated on the surface of the paper and dried to obtain the fluorescently brightened paper. To be more specific, the coating liquid can be prepared usually by adding 5–30 parts by mass of adhesive, 0.05–10 part(s) by mass of the aqueous liquid composition of the present invention, 0.1–0.5 part by mass of dispersing agent and water to 100 parts by mass of white inorganic pigment so as to adjust the content of the solid in the mixture to 40–70% by mass. That is applied on the surface of the paper prepared as above using a coater or a gate roll to make usually 5–40 g/m$^2$ (dry mass) and dried by, for example, a hot-air drier usually at 90–130° C. to give fluorescently brightened paper. If desired in that case, a water-resisting agent of resin of a polyamide-urea type, resin of a melamine type, or antiseptic agent and an anti-foaming agent thereto may be added. As an adhesive, a mixture of modified starch (such as oxidized starch, phosphated starch and enzymatically modified starch) with a styrene-butadiene copolymer (for example, a mixture of modified starch with styrene-butadiene copolymer in a ratio by mass of 1–6:4–9), polyvinyl alcohol, etc. are usually used. With regard to the white inorganic pigment, a clay, kaolin, a heavy calcium carbonate, a light calcium carbonate, a titanium oxide, an aluminum hydroxide and an amorphous silica gel and they may be used in combination. As the dispersing agent, a polymer of an acrylate type, a sodium pyrophosphate, a sodium tripolyphosphate, etc. may be used by conventional method.

In the case of overcoating in an external addition method for recording paper having a receiving layer for ink jet, pulp is firstly beaten to a predetermined beaten degree with a pulper, a refiner or the like to make a pulp sulurry, then a usual filler, a sizing agent, a sulfate band, a fixing agent, etc. are appropriately added thereto and subjected to paper manufacture by conventional method as same as above. A coating liquid containing the aqueous liquid composition of the present invention is applied on the surface of the paper and dried to obtain the fluorescently brightened paper. To be more specific, the coating liquid can be prepared usually by adding 5–30 parts by mass of adhesive, 0.05–10 part(s) by mass of the aqueous liquid composition of the present invention, 0.1–0.5 part by mass of dispersing agent, 0.50–30 part(s) by mass of cationic ink fixing agent and water to 100 parts by mass of white inorganic pigment so as to adjust the content of the solid in the mixture to 40–70% by mass. That is applied on the surface of a paper with a coater or a gate roll in amount of usually 5–40 g/m² (dry mass) and dried by, for example, a hot-air drier usually at 90–130° C. to obtain fluorescently brightened paper. The receiving layer may be made in a layered constitution having two or more layers. It is also possible to apply a paint for luster layer on the ink receiving layer.

The cationic ink fixing agent used for the coating liquid includes higher aliphatic amine, a compound of a quaternary ammonium salt type, an ethylene oxide adduct of secondary alkylamine, a cationic polymer compound, inorganic particles where the surface is cationic, etc. The higher aliphatic amine, includes compounds of primary to tertiary amine salt type, more specifically, hydrochloride, acetate, etc. of laurylamine, coconut amine, stearylamine, rosin amine, etc. With regard to the compound of a quaternary ammonium type, there may be listed lauryltrimethylammonium chloride, lauryldimethylbenzylammonium chloride, benzyltributylammonium chloride, benzalkonium chloride, cetyltrimethylammonium chloride, etc.; further includes compounds of a pyridinium base type, more specifically, cetylpyridinium chloride, cetylpyridinium bromide, etc.; further includes cationic compounds of an imidazoline type or, more specifically, 2-heptadecenyl-hydroxyethylimidazoline. As the ethylene oxide adduct of secondary alkylamine, dihydroxyethylstearylamine may be listed.

The cat ionic polymer compound used as a cationic ink fixing agent includes polyacrylamide, polyallylamine, polyaminesulfone and polyvinylamine or, more specifically, aminomethyl acrylamide copolymer, polydiallyldimethylammonium chloride, quaternary ammonium base-containing alkyl acrylate, etc. Further, it includes a cationic polymer such as cationized starch, chitosan neutralized product or partially neutralized product thereof with an acid such as hydrochloride, acetate, etc; a cationic polymer compound comprising dimethylamine-epichlorohydrin polycondensate, acrylamide-diallylamine copolymer, polyvinylamine copolymer, dicyandiamide and dimethyl-diallyl-ammonium chloride as a main component.

The inorganic particles where surface is cationic used as a cationic ink fixing agent, include, for example, fine particles of alumina and silica particles where a compound having both cationic group and a group which is able to react with the silica particle surface is made to react therewith.

Amount of such a cationic substance when applying to paper is about 0.1–10 g/m², preferably, about 0.5–5 g/m².

The aqueous liquid composition of the present invention is excellent in storage stability at low and high temperatures in the coexistence of inorganic salt which is produced upon synthesis and also in a state of the synthesized sodium salt, etc. without the removal of inorganic salt, the conversion to lower alkanolamine salt and lower alkyl quaternary ammonium salt, or the addition of solubilizing agent such as urea to enhance the stability of the solution. Moreover, the paper which is fluorescently brightened by the aqueous liquid composition of the present invention does not cause a quenching phenomenon and is hardly influenced by quality of paper or by changes in composition of size press liquid and coating liquid and shows excellent whiteness. Furthermore, it gives excellent whiteness even when used in combination with cationic ink fixing agent or water-resisting agent which is usually used in recording paper for ink jet printers.

EXAMPLES

As hereunder, the present invention will be illustrated in more detail by way of Examples although the present invention is not limited to those Example.

(Synthetic Examples and Test for Storage Stability of the Aqueous Liquid Composition)

Example 1

Cyanuric chloride (20 parts by mass) was dispersed using 80 parts by mass of water, 40 parts by mass of ice and 0.1 part by mass of a nonionic dispersing agent. To this dispersion were added 32.7 parts by mass of aniline-2,5-disulfonic acid. Temperature was lowered down to 5° C. by adding ice and then raised from 5.0° C. to 25° C. taking 3 hours and keeping the pH 4.0–4.5 by addition of a sodium hydroxide solution. An aqueous solution (130 parts by mass) dissolving 19.5 parts by mass of 4,4'-diaminostilbene-2,2'-disulfonic acid were dissolved and being adjusted to pH 9.5–10.5 by sodium hydroxide was added dropwise thereinto taking 3 hours. During that period, a sodium hydroxide solution was added so as to keep the pH 4.0–4.5 and temperature was gradually raised from 35° C. to 50° C. Di-2-propanolamine (18 parts by mass) was added to the solution to react for 3 hours at 80° C. keeping the pH 8.5–9.0 by addition of a sodium hydroxide solution. The resulting reaction solution contained 15% by mass of the compound represented by the formula (2). To the resulting reaction solution was added hydrochloric acid to adjust to pH 0.6 and the precipitated crystals were filtered to give a free acid (M=H) of the compound of the formula (2). Water (80 parts by mass) was added to 50 parts by mass of the crystals containing water and pH was adjusted to 8.5 by sodium hydroxide to obtain an aqueous liquid composition of the present invention containing 15% by mass of sodium salt of the compound represented by the formula (2). Although the composition contained 1.8% by mass of inorganic salt, crystals of the fluorescent brightener were not separated out but a stably dissolved state was maintained even after it was stored at −5° C. and 40° C. for two months (λmax in water was 348 nm).

Example 2

The reaction solution which was prepared in the same manner as in Example 1 was cooled at 50° C., 80 parts by mass of sodium chloride were added and the precipitated crystals were filtered to obtain sodium salt (M=Na) of the compound of the formula (2). Water was added to 50 parts by mass of the water-containing crystals to obtain an aqueous liquid composition of the present invention containing 20% by mass of sodium salt of the compound represented by the formula (2). Although the composition contained 2.0% by mass of inorganic salt, crystals of the fluorescent brightener were not separated out but a stably dissolved state was maintained even after it was stored at −5° C. and 40° C. for two months.

Example 3

The reaction solution obtained in Example 1 contained 15% by mass of sodium salt (M=Na) of the compound represented by the formula (2). Although the composition contained 4.5% by mass of inorganic salt, crystals of the fluorescent brightener were not separated out but a stably dissolved state was maintained even after it was stored at −5° C. and 40° C. for two months.

Comparative Example 1

Cyanuric chloride (20 parts by mass) was dispersed using 80 parts by mass of water, 40 parts by mass of ice and 0.1 part by mass of nonionic dispersing agent. To the dispersion were added 32.7 parts by mass of aniline-2,5-disulfonic acid. Temperature was cooled down to 5° C. by adding of ice and then raised from 5° C. to 25° C. taking 3 hours and keeping the pH 4.0–4.5 by addition of a sodium hydroxide solution. An aqueous solution (130 parts by mass) dissolving 19.5 parts by mass of 4,4'-diaminostilbene-2,2'-disulfonic acid and adjusted to pH 9.5–10.5 by sodium hydroxide was added dropwise into the solution taking 3 hours. During that period, a sodium hydroxide solution was added to adjust the pH to 4.0–4.5 and temperature was gradually raised from 35 to 50° C. To the solution were added 14 parts by mass of diethanolamine and the reaction was carried out at 80° C. for 3 hours keeping the pH at 8.5–9.0 by addition of a sodium hydroxide solution. To the resulting reaction solution were added 80 parts by mass of sodium chloride and the precipitated crystals were filtered to obtain a compound represented by the following formula (3) (the compound of Example 19 of Belgian Patent 719065). To 50 parts of the water-containing crystals was added water (100 parts by mass) to prepare a solution containing 15% by mass of the compound represented by the following formula (3). The solution contained 2.1% by mass of inorganic salt and, when this was stored at −5° C., crystals were separated out on the first day.

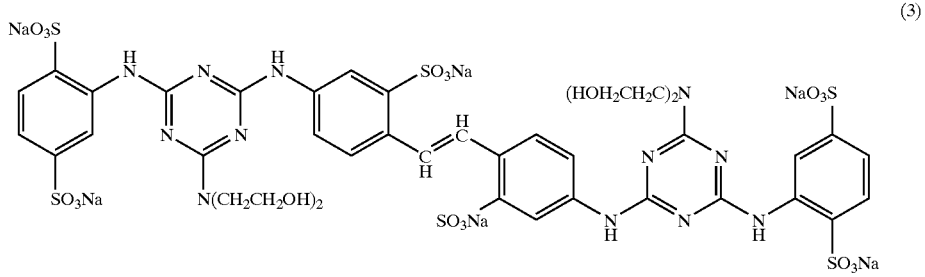

(3)

Comparative Example 2

Cyanuric chloride (20 parts by mass) was dispersed using 80 parts by mass of water, 40 parts by mass of ice and 0.1 part by mass of nonionic dispersing agent. To the dispersion were added 32.7 parts by mass of aniline-2,5-disulfonic acid. Temperature was cooled down to 5° C. by addition of ice and then raised from 5° C. to 25° C. taking 3 hours and keeping the pH 4.0–4.5 by adding of a sodium hydroxide solution. An aqueous solution (130 parts by mass) dissolving 19.5 parts by mass of 4,4'-diaminostilbene-2,2'-disulfonic acid and adjusted to pH 9.5–10.5 by sodium hydroxide was added dropwise into the solution taking 3 hours. During that period, a sodium hydroxide solution was added to adjust the pH to 4.0–4.5 and the temperature was gradually raised to 35 to 50° C. To the solution were added 10 parts by mass of 2-propanolamine and the reaction was carried out at 80° C. for 3 hours keeping the pH at 8.5–9.0 by adding of a sodium hydroxide solution. To the resulting reaction solution were added 80 parts by mass of sodium chloride and the precipitated crystals were filtered to obtain a compound represented by the following formula (4) (the compound of Example 7 of Belgian Patent 719065). To 50parts of the water-containing crystals was added water (100 parts by mass) to prepare a solution containing 15% by mass of the compound represented by the following formula (4). The solution contained 2.0% by mass of inorganic salt and, when this was stored at −5° C., crystals were separated out on the third day.

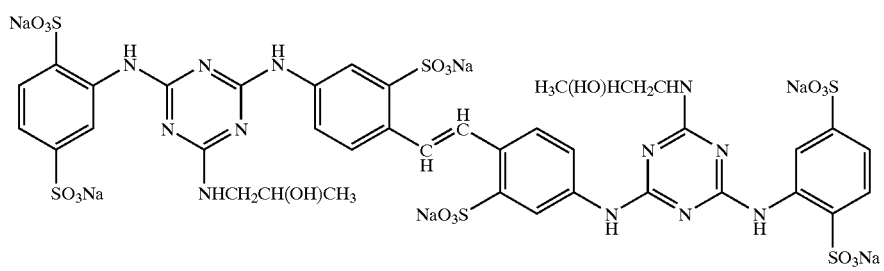

(4)

From those results, it is noted that the aqueous liquid composition using the compound represented by the formula (2) of the present invention is excellent in storage stability even if much inorganic substance is contained.

(Dyeing Examples: Overcoating in External Addition Method)

Example 4

Water was added to a mixture comprising 20 parts of the aqueous liquid composition prepared in Example 1, 800 parts of clay, 200 parts of heavy calcium carbonate, 3 parts of dispersing agent of an acrylic type (trade name: Kayacryl Resin C-220N, manufactured by NIPPON KAYAKU KABUSHIKI KAISHA), 50 parts of phosphated starch (trade name: MS-4600, manufactured by Nippon Shokuhin Kako), 120 parts of latex (copolymer of styrene and butadiene, L-1622 (trade name), manufactured by Asahi Kasei) and 4 parts of water-proofing agent (Sumirez Resin 636 (trade name), manufactured by Sumitomo Chemical) to prepare a coating liquid where solid content was 55%. This was coated on paper of high quality and dried at 120° C. and the result of measurement of the color using a spectrocolorimeter for whiteness (trade name: SC-10W, manufactured by Suga Shikenki) is shown in Table 1. Incidentally, degree of whiteness was determined in accordance with JIS P 8148.

Comparative Example 3

The same method as in Example 4 was carried out except that the aqueous liquid composition prepared in Comparative Example 1 was used instead of the aqueous liquid composition prepared in Example 1 to prepare a fluorescently brightened paper and the result of measurement of the color is shown in Table 1.

Comparative Example 4

The same method as in Example 4 was carried out except that the aqueous liquid composition prepared in Comparative Example 2 was used instead of the aqueous liquid composition prepared in Example 1 to prepare a fluorescently brightened paper and the result of measurement of the color is shown in Table 1.

TABLE 1

| Degree of Whiteness (ΔW) | |
|---|---|
| Example 4 | 27.0 |
| Comparative Example 3 | 25.6 |
| Comparative Example 4 | 25.3 |

From those results, it is noted that Example 4 shows high degree of whiteness and that the aqueous liquid composition using the compound represented by the formula (2) of the present invention is excellent in fluorescently brightening ability.

(Dyeing Examples: Size Press in External Addition Method)

Example 5

Anionic surface sizing agent (trade name: Polymaron 382, manufactured by Arakawa Kagaku) (4 parts) was added to an aqueous solution comprising 20 parts of the aqueous liquid composition prepared in Example 1 and 976 parts of 3% oxidized starch (trade name: MS-3800, manufactured by Nippon Shokuhin Kako) to prepare a sizing coating liquid. The liquid was fed to a size press machine, coated on a weakly sized paper where Steckihit size of 7 seconds and dried at 65° C. to 70° C., the resulting fluorescently brightened paper was subjected to color measurement using a spectrocolorimeter for whiteness (trade name: SC-10W, manufactured by Suga Shikenki) and the result is shown in Table 2.

Comparative Example 5

The same method as in Example 5 was carried out except that the aqueous liquid composition prepared in Comparative Example 1 was used instead of the aqueous liquid composition prepared in Example 1 to prepare a fluorescently brightened paper and the result of measurement of the color is shown in Table 2.

Comparative Example 6

The same method as in Example 5 was carried out except that the aqueous liquid composition prepared in Comparative Example 2 was used instead of the aqueous liquid composition prepared in Example 1 to prepare a fluorescently brightened paper and the result of measurement of the color is shown in Table 2.

TABLE 2

| Degree of Whiteness (ΔW) | |
| --- | --- |
| Example 5 | 60.8 |
| Comparative Example 5 | 58.6 |
| Comparative Example 6 | 59.6 |

From those results, it is noted that Example 5 shows high degree of whiteness and that the aqueous liquid composition using the compound represented by the formula (2) of the present invention is excellent in fluorescently brightening ability.

(Overcoating in the External Addition Method Using a Coating Liquid for the Receiving Layer for Ink Jet Recording Paper)

Example 6

A coating liquid for receiving layer was prepared so as to make concentration of the coating liquid (solid) 13% using 100 parts of superfine powder of silica (manufactured by Mizusawa Kagaku Kogyo; trade name: Mizukasil P-78A), 30 parts of polyvinyl alcohol (manufactured by Nippon Gosei Kagaku; trade name: Gosenol NM-11), 10 parts of solid of polydiallyldimethylammonium chloride (quaternary ammonium salt of polymer) which was a cationic dye fixing agent (manufactured by Senka; trade name: HP-126A) and 6 parts of the aqueous liquid composition prepared in Example 1. This coating liquid for ink receiving layer was applied to commercially available neutral PPC paper using a bar coater so as to have dry mass of 5 g/m² and dried at 120° C. to prepare fluorescently brightened paper having a receiving layer and the result of color measurement is shown in Table 3.

Comparative Example 7

The same operation as in Example 6 was carried out except that the aqueous liquid composition prepared in Comparative Example 1 was used instead of the aqueous liquid composition prepared in Example 1 to prepare a fluorescently brightened paper having a receiving layer and the result of measurement of the color is shown in Table 3.

Comparative Example 8

The same operation as in Example 6 was carried out except that the aqueous liquid composition containing 15% by weight of a fluorescent brightener represented by the following formula (5)

was used instead of the aqueous liquid composition prepared in Example 1 to prepare a fluorescently brightened paper having a receiving layer and the result of measurement of the color is shown in Table 3.

TABLE 3

| Degree of Whiteness (ΔW) | |
| --- | --- |
| Example 6 | 38.9 |
| Comparative Example 7 | 33.3 |
| Comparative Example 8 | 33.2 |

In the conventionally used anionic fluorescent brighteners, there is a disadvantage that it is combined with quaternary ammonium salt, etc. of polymer used for the ink receiving paper and crystals are separated out or that degree of whiteness of the coated paper is deteriorated. However, from the above results, it is noted that Example 6 shows high degree of whiteness and that the aqueous liquid composition using the compound represented by the formula (2) of the present invention is excellent in fluorescently brightening ability especially when jointly used with quaternary ammonium salt, etc. of polymer.

INDUSTRIAL APPLICABILITY

The aqueous liquid composition of the present invention is excellent in storage stability at low and high temperatures without the removal of inorganic salt, the conversion to lower alkanolamine salt or lower alkyl quaternary ammonium salt to enhance the stability of the liquid and the addition of solubilizing agent such as urea. Thus, the aqueous liquid composition of the present invention is a stable aqueous liquid composition containing the compound of the formula (1) in a high concentration even in the co-existence of inorganic salt which is produced upon synthesis and, as compared with fluorescent brighteners containing the conventional stilbene derivative in a high concentration, it can be easily manufactured and, in addition, it shows an excellent whitening effect when cellulose such as paper, pulp or cotton is subjected to fluorescent brightening. It furthermore is excellent in fluorescent brightening ability even when used together with quaternary ammonium salt of ink fixing agent polymer which is used particularly for ink receiving paper and is quite useful as a fluorescent brightener. Accordingly, its industrial value is very high.

The invention claimed is:

1. A method for fluorescent brightening of ink jet recording paper, comprising applying to said paper an aqueous (5)

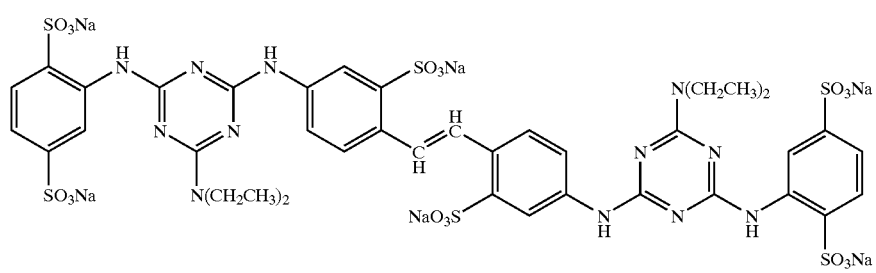

liquid composition comprising 10–40% by mass of an alkali salt of a compound represented by the following formula (2) in a form of free acid:

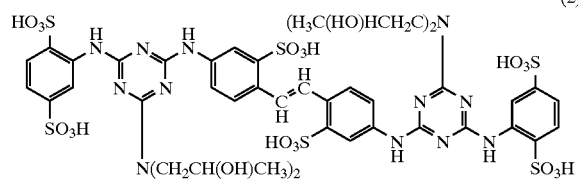

(2)

and 1.1–10% by mass of inorganic salt, together with cationic ink fixing agent.

2. The method for fluorescent brightening of ink jet recording paper according to claim 1, wherein said alkali salt is alkaline metal salt, alkaline earth metal salt or ainmonium salt.

3. The method for fluorescent brightening of ink jet recording paper according to claim 1, wherein said liquid composition salt contains substantially no organic solvent and no solubilizer.

* * * * *